United States Patent
Olivio et al.

(10) Patent No.: US 10,370,961 B2
(45) Date of Patent: Aug. 6, 2019

(54) DOWNHOLE TOOL AND ELECTRONICS PACKAGING CONFIGURATION THEREFOR

(71) Applicant: Schlumberger Technology Corporation, Sugar Land, TX (US)

(72) Inventors: Amanda Olivio, Tomball, TX (US); Gary A. Hazen, Houston, TX (US); Fernando Garcia-Osuna, Sugar Land, TX (US); Robert Monroe Lowe, Jr., Katy, TX (US); Jason Guernsey, Katy, TX (US); Tao Xu, Houston, TX (US); Michael C. Sakach, Sugar Land, TX (US); Mark A. Fredette, Houston, TX (US); Ricardo Y. Torres, Manvel, TX (US); Arturo Mejia, Sugar Land, TX (US); Mia Pommier, Sugar Land, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 15/563,626

(22) PCT Filed: Apr. 4, 2016

(86) PCT No.: PCT/US2016/025812
§ 371 (c)(1),
(2) Date: Oct. 2, 2017

(87) PCT Pub. No.: WO2016/161411
PCT Pub. Date: Oct. 6, 2016

(65) Prior Publication Data
US 2018/0073354 A1 Mar. 15, 2018

Related U.S. Application Data

(60) Provisional application No. 62/142,343, filed on Apr. 2, 2015.

(51) Int. Cl.
*G01V 3/00* (2006.01)
*E21B 47/12* (2012.01)
(Continued)

(52) U.S. Cl.
CPC .......... *E21B 47/122* (2013.01); *E21B 47/011* (2013.01); *G01N 27/302* (2013.01);
(Continued)

(58) Field of Classification Search
CPC .. G01R 31/3658; G01N 31/02; G01N 27/302; G01N 27/4165; G01N 31/221
(Continued)

(56) References Cited

U.S. PATENT DOCUMENTS 4,547,833 A 10/1985 Sharp
2002/0195247 A1* 12/2002 Ciglenec ........... E21B 7/06
166/250.11
(Continued)

FOREIGN PATENT DOCUMENTS

WO WO2013134176 A1 9/2013

OTHER PUBLICATIONS

International Search Report and Written Opinion issued in International Patent Application PCT/US2016/025812 dated Jul. 14, 2016. 18 pages.

Primary Examiner — Huy Q Phan
Assistant Examiner — Raul J Rios Russo

(57) ABSTRACT

A tool for use in a borehole in a geological formation may include a chassis, a drill collar surrounding the chassis, a port plug coupled between the drill collar and the chassis, RF antennas carried by the drill collar, and a multi-chip module (MCM) electronics package(s). The electronics package(s) may include a hermetically sealed electronics housing positioned between the chassis and the drill collar, a substrate within the electronics housing, RF transmitter
(Continued)

circuitry on the substrate to cooperate with at least one first RF antenna to transmit RF signals into the geological formation, and RF receiver circuitry on the substrate to cooperate with at least one second RF antenna to receive RF signals from the geological formation. Furthermore, an electronics housing mount may couple the electronics housing with the port plug, and the electronics housing mount may have a passageway extending therethrough for receiving the port plug.

22 Claims, 4 Drawing Sheets

(51) Int. Cl.
| | |
|---|---|
| G01N 31/02 | (2006.01) |
| G01N 27/416 | (2006.01) |
| G01N 27/30 | (2006.01) |
| E21B 47/01 | (2012.01) |
| G01V 3/30 | (2006.01) |
| G01R 27/00 | (2006.01) |

(52) U.S. Cl.
CPC ......... *G01N 27/4165* (2013.01); *G01N 31/02* (2013.01); *G01V 3/30* (2013.01); *G01R 27/00* (2013.01)

(58) Field of Classification Search
USPC ........ 324/323, 332, 333, 338, 346, 351, 376
See application file for complete search history.

(56) References Cited

U.S. PATENT DOCUMENTS

| | | |
|---|---|---|
| 2005/0150691 A1 | 7/2005 | Schultz et al. |
| 2013/0043874 A1* | 2/2013 | Clark ...................... E21B 10/00 324/369 |
| 2013/0087903 A1 | 4/2013 | Cherchali et al. |
| 2013/0099935 A1 | 4/2013 | Ujereh et al. |
| 2013/0255966 A1* | 10/2013 | Palaghita .............. E21B 47/122 166/378 |
| 2014/0176139 A1* | 6/2014 | Espinosa .................. G01V 3/12 324/333 |
| 2015/0101867 A1* | 4/2015 | Clark ...................... E21B 10/00 175/50 |
| 2017/0044893 A1* | 2/2017 | Derkacz ................ E21B 47/011 |

* cited by examiner

DOWNHOLE TOOL AND ELECTRONICS PACKAGING CONFIGURATION THEREFOR

CROSS-REFERENCE TO RELATED APPLICATIONS

This application claims priority to U.S. Provisional Application 62/142,343 dated Apr. 2, 2015, the entirety of which is incorporated by reference.

BACKGROUND

Logging while drilling (LWD) or measurement while drilling (MWD) systems are used to monitor downhole conditions while drilling for hydrocarbon resources, such as oil or natural gas. By way of example, LWD/MWD systems may include one or more sensors which measure formation properties such as density, resistivity, gamma rays, porosity, etc. Other sensors may also be included to measure selected drilling parameters, such as inclination and azimuth trajectory of the wellbore, for example. Additional drilling sensors may include a sensor for measuring axial force (weight) applied to the LWD/MWD system, and shock and vibration sensors.

With respect to resistivity tools, these generally include an array of radio frequency (RF) transmitters and receivers, which are respectively used to transmit RF signals into the formation and receive the reflected RF energy, which may then be used to determine resistivity measurements for the formation. The transmitters and receivers electronics package is generally made of a conductive and/or magnetic material for electromagnetic shielding purposes. In addition, it may be desirable for the electronics package to maintain good electrical and mechanical contact with the drill collar to reduce noise, which affects the resistivity measurement. Yet, the stresses and high operating temperatures experienced in a borehole environment may still lead to problems with electronic components in resistivity tools, as well as other downhole tools, in some instances.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

A tool for use in a borehole in a geological formation may include a chassis, a drill collar surrounding the chassis, a port plug coupled between the drill collar and the chassis, a plurality of radio frequency (RF) antennas carried by the drill collar, and at least one multi-chip module (MCM) electronics package. The at least one MCM electronics package may include a hermetically sealed electronics housing positioned between the chassis and the drill collar, a substrate within the hermetically sealed electronics housing, RF transmitter circuitry on the substrate to cooperate with at least one first RF antenna from among the plurality of RF antennas to transmit RF signals into the geological formation, and RF receiver circuitry on the substrate to cooperate with at least one second RF antenna from among the plurality of RF antennas to receive RF signals from the geological formation. Furthermore, an electronics housing mount may couple the hermetically sealed electronics housing with the port plug, and the electronics housing mount may have a passageway extending therethrough to receive the port plug.

DETAILED DESCRIPTION

The present description is made with reference to the accompanying drawings, in which example embodiments are shown. However, many different embodiments may be used, and thus the description should not be construed as limited to the embodiments set forth herein. Rather, these embodiments are provided so that this disclosure will be thorough and complete. Like numbers refer to like elements throughout, and prime notation is used to indicate similar elements in different embodiments.

Figure 1:
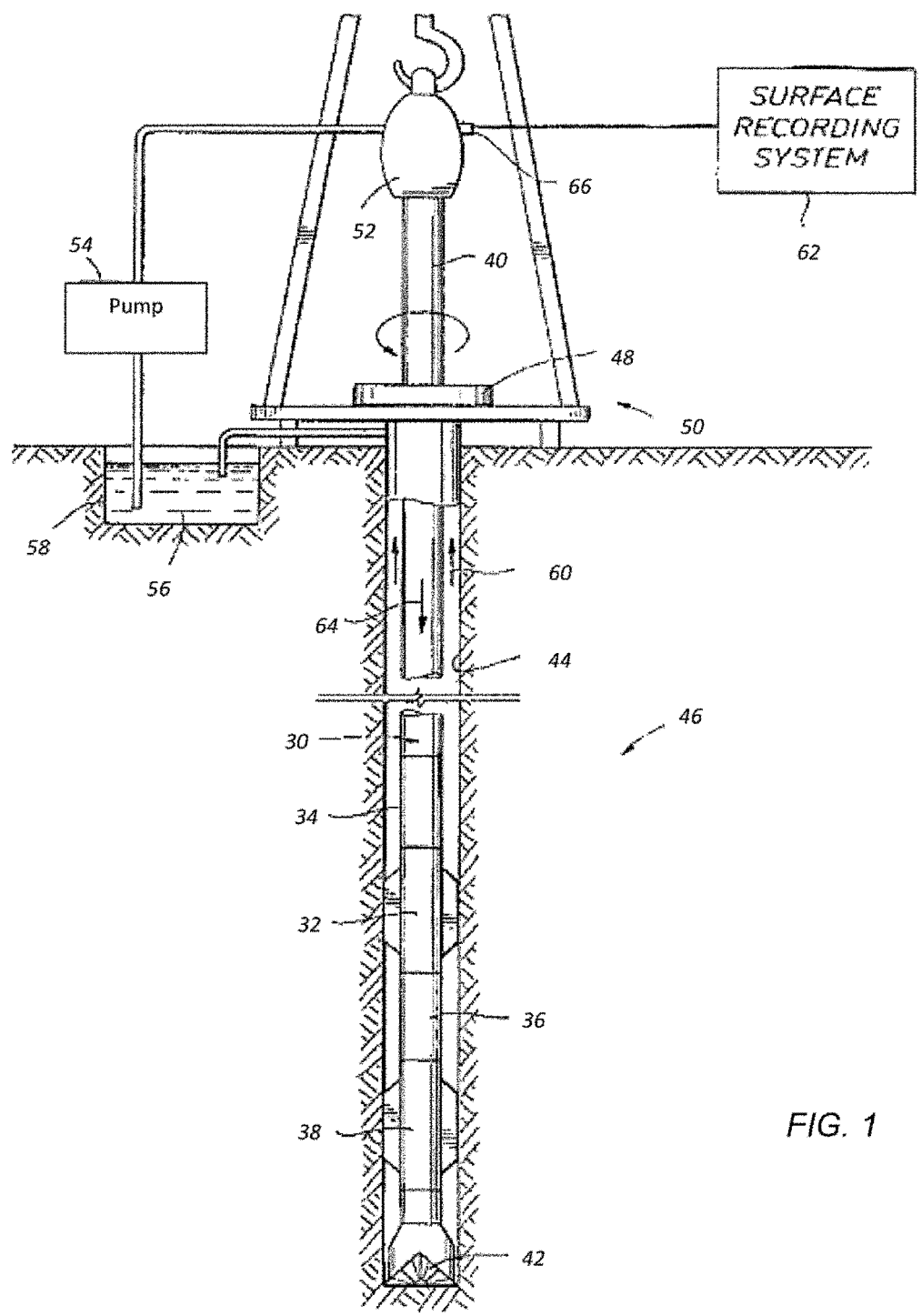
FIG. 1 is a schematic diagram illustrating a wellbore logging while drilling (LWD) system in which example LWD tool electronic assembly embodiments may be used.

Referring initially to FIG. 1, an example approach for a well-logging application, such as for hydrocarbon resource (e.g., oil, natural gas, etc.) wells, is first described. The example shown in FIG. 1 is for a logging while drilling (LWD) or measurement while drilling (MWD) implementation. In the illustrated embodiment, an example configuration for acquiring well log data using an LWD/MWD system 30 is shown. The LWD/MWD system 30 illustratively includes one or more collar sections 32, 34, 36, 38 coupled to the lower end of a drill pipe 40. The LWD/MWD system 30 includes a drill bit 42 at the bottom end to drill the wellbore or borehole 44 through the earth or geological formation 46. In this example, drilling is performed by rotating the drill pipe 40 using a rotary table 48. However, drilling may also be performed by other suitable approaches, such as top drives and coiled tubing drilling with downhole motors, for example.

During rotation, the pipe 40 is suspended by equipment on a drill rig 50 including a swivel 52, which enables the pipe 40 to rotate while maintaining a fluid tight seal between the interior and exterior of the pipe 40. Mud pumps 54 draw drilling fluid, such as oil-based med (OBM) or simply "mud", 56 from a tank or pit 58 and pump the OBM through the interior of the pipe 40, down through the LWD/MWD system 30, as indicated by arrow 64. The mud 56 passes through orifices (not shown) in the bit 42 to lubricate and cool the bit 42, and to lift drill cuttings in through an annulus 60 between the pipe 40 and the wellbore 44.

The collar sections 32, 34, 36, 38 may include sensors (not shown) therein which make measurements of various properties of the geological formation 46 through which the wellbore 44 is drilled. These measurements may be recorded in a recording device disposed in one or more of the collar sections 32, 34, 36, 38, or communicated to a surface recording system 62 outside of the well. For example, MWD systems may also provide the telemetry (communication system) for any MWD/LWD tool sensors in the drill string. By way of example, the controller 62 may be implemented using a combination of hardware (e.g., microprocessor, etc.), and a non-transitory computer-readable medium having computer executable instructions for performing the various operations noted herein.

Example LWD systems include one or more sensors which measure formation properties such as density, resistivity, gamma rays, porosity, etc., as will be described further below. Other sensors may also be included to measure selected drilling parameters, such as inclination and azimuth trajectory of the wellbore 44, for example. Additional drilling sensors may include a sensor for measuring axial force (weight) applied to the LWD/MWD system 30, and shock and vibration sensors.

The LWD/MWD system 30 may further include a mud pressure modulator (not shown separately) in one of the collar sections (e.g., the collar section 34). The modulator applies a telemetry signal to the flow of mud 56 inside the system 30 and pipe 40 where the telemetry signal is detected by a pressure sensor 66 disposed in the mud flow system. The pressure sensor 66 is coupled to detection equipment in a surface recording system 62, which enables recovery and recording of information transmitted in the telemetry scheme sent by the MWD portion of the LWD/MWD system 30. The telemetry scheme may include a subset of measurements made by the various sensors in the LWD/MWD system 30. The telemetry of the logging tools may also be determined using a wireline cable, or electrical MWD telemetry (e.g., using electrical signals transmitted through the formation). Measurements made by the various sensors in the LWD/MWD system 30 may also be transferred to the surface recording system 62 when the LWD/MWD system 30 is withdrawn from the wellbore.

Turning to FIGS. 2-5, an electronics assembly 100 which may be used with one or more of the LWD tools in the tool string shown in FIG. 1, e.g., a resistivity measurement tool, is now described. Generally speaking, the electronics assembly 100 provides a hybrid multichip module (MCM) configuration for downhole resistivity tool transmitter and receiver electronics (or other downhole tool electronics) enabling reliable high temperature operation. By way of background, in certain resistivity tools, such as arcVISION, PeriScope, GeoSphere, EcoScope, and Impulse from the present Applicant Schlumberger Limited, electromagnetic shielding and low noise operation may be achieved using printed circuit board (PCB) technology enclosed in gold plated, beryllium copper packages which are mounted to the drill collar via a port plug. Yet, PCB configurations may be susceptible to reliability issues in some high temperature applications.

Other approaches to downhole tool electronics assemblies use hybrid MCM configurations in which high temperature co-fired ceramic (HTCC) hybrid MCMs with die components are hermetically sealed. This approach may provide enhanced reliability at high temperatures. Such packages include a housing, ceramic substrate, hermetic connector, and lid which seals the electronics inside the package. However, to meet desired electromagnetic and noise requirements, such hybrid electronic packages for the transmitter and receiver are usually mounted to the collar, similar to a PCB package configuration.

The electronics assembly 100 may provide advantages of both PCB and hybrid MCM mounting configurations. More particularly, the electronics assembly 100 is mounted within a tool 101 (which is a resistivity measurement tool in the illustrated example) including a chassis 102, a drill collar 103 surrounding the chassis, a port plug 104 coupled between the drill collar and the chassis, and a plurality of radio frequency (RF) antennas 105 carried by the drill collar. In the example embodiment, the electronics assembly 100 illustratively includes a pair of first and second MCM electronics packages 106, 107, and an electronics housing mount 108 coupled between the first and second MCM electronics packages.

Figure 2:
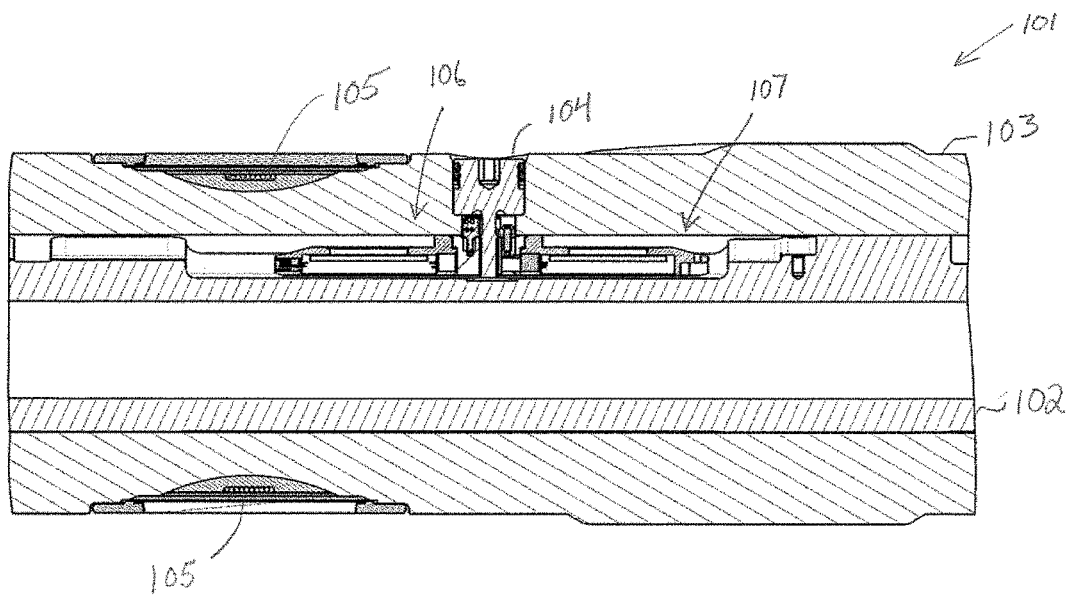
FIG. 2 is a cross-sectional view of a portion of a resistivity measurement tool which may be used with the LWD system of FIG. 1, and more particularly illustrating an electronics assembly embodiment therefor.
Figure 3:
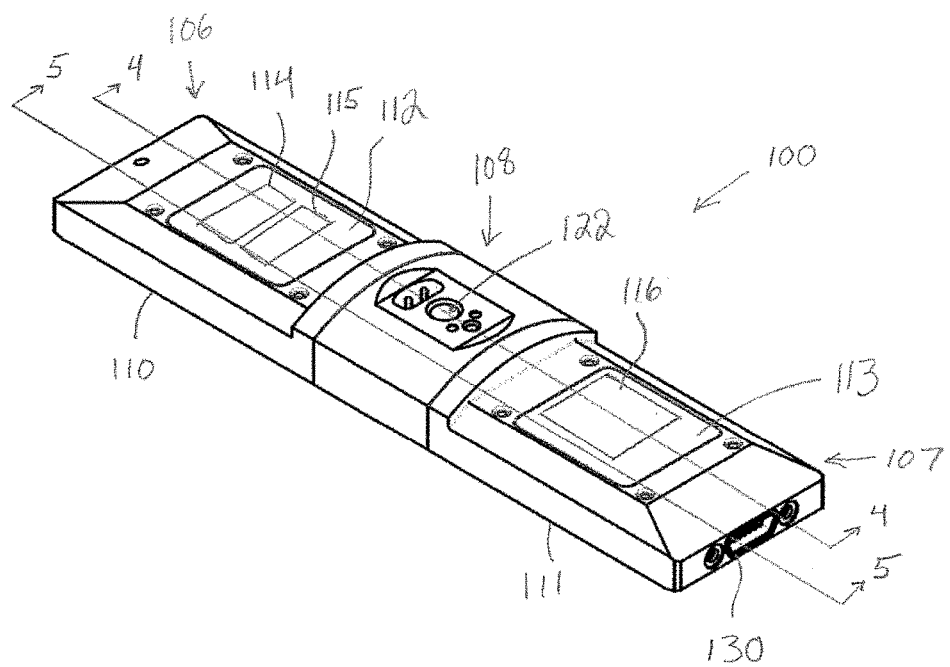
FIG. 3 is a perspective view of the electronics assembly shown in FIG. 2.
Figure 4:
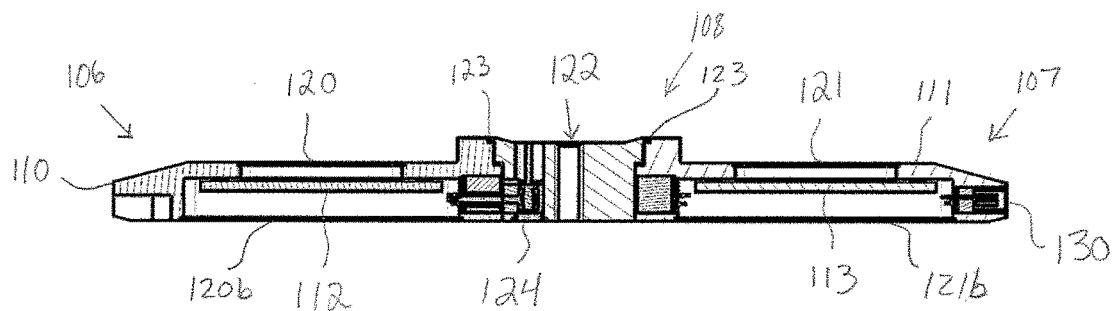
FIGS. 4 and 5 are cross-sectional side views of the electronics assembly of FIG. 3, taken along lines 4-4 and 5-5, respectively.
Figure 5:
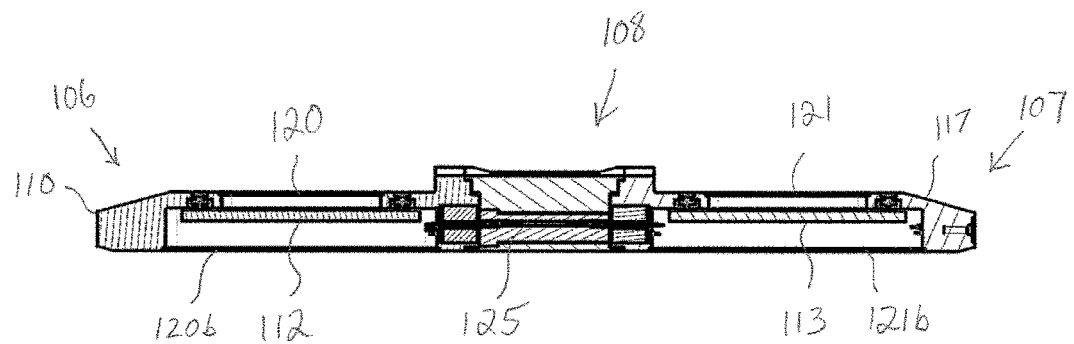

Each of the MCM electronics packages 106, 107 may include an electronics housing 110, 111, which are to be positioned between the chassis 102 and the drill collar 103, as seen in FIG. 2. A respective substrate 112, 113 is positioned within each electronics housing 110, 111. In particular, the substrates 112, 113 may be ceramic substrates, such as HTCC substrates, for example, although other suitable ceramics or materials which are suitable for high temperature applications while providing desired shock or vibration performance may also be used. RF transmitter circuitry 114 and RF receiver circuitry 115 are mounted on the substrate 112 to cooperate with one or more of the RF antennas 105 to transmit RF signals into the geological formation 46 and receive reflected RF signal energy from the geological formation, as noted above.

In the illustrated example, digital control circuitry 116 (e.g., microprocessor, memory, etc.) for the electronics assembly 100 is mounted on the substrate 113, and is thereby isolated from the analog RF components in the first housing 106 to provide enhanced performance, although the various digital and analog components may be intermixed between the first and second packages 106, 107 in different embodiments. More particularly, the centered hybrid package arrangement allows for the digital control circuitry 116 and the RF transmitter/receiver circuitry 114, 115 to be separated, enabling the isolation of high-sensitivity small level RF signals, for example. The control circuitry 116 may cooperate with the RF transmitter circuitry 114 and the RF receiver circuitry 115 to determine resistivity measurements for the geological formation 46, as well as communicate with the surface recording system 62 and/or other tools in the tool string, for example. To this end, a hermetic connector 130 is illustratively carried by the second housing 111 and is coupled with digital control circuitry 116 on the substrate 113.

It should be noted that while the RF transmitter and receiver circuitry 114, 115 are illustratively shown as separate components in the illustrated example, in some embodiments the RF circuitry components may all be incorporated in a common transceiver chip or package (or this circuitry may be split among more than two components). Respective lids 120, 121 and 120*b*, 121*b* hermetically seal openings in front and back sides of the first and second housings 110, 111 to protect the RF transmitter and receiver circuitry 114, 115 and the digital control circuitry 116 therein. The lids 120, 120*b*, 121 and 121*b* may also be made from a similar material to the electronic housing 110 and 111, although other suitable materials may also be used.

The electronics housing mount 108 couples the hermetically sealed electronics packages 106, 107 with the port plug 104, and the electronics housings are symmetrically mounted on opposite sides of the electronics housing mount in a "centered" arrangement. Since each of the electronics packages 106, 107 are independently hermetically sealed, this allows the electronics housing mount 108 to be non-hermetic. The electronics housing mount 108 has a passageway 122 extending therethrough for receiving the port plug 104. One or more antenna connectors 124 (FIG. 4) are carried by the housing mount 108 and connect the RF transmitter and receiver circuitry 114, 115 with respective antennas 105. However, it should be noted that wireless communication links may be used between the RF transmitter and receiver circuitry 114, 115 and the antennas 105 in some embodiments.

The electronics housings 106, 107 may be manufactured of materials compatible with the ceramic substrates 112, 113, that is, having a similar coefficient of thermal expansion, such as titanium or Kovar, for example. The housing mount 108 may be manufactured of materials with sufficient strength to withstand the torque required to secure the electronics assembly 100 within the tool 101 via the port plug 104, such as a metal. A metal housing mount 108 not only provides desired strength and rigidity, but this also allows for a welded connection 123 with the first and second housings 110, 111. The housing mount 108 further illustratively includes one or more feed-through connectors 125 which are coupled between the first and second housings 110, 111. By way of example, a pair of feed-through connectors 125 may be provided on opposing sides of the passageway 122 (not shown), although other numbers of feed-through connectors may be used in different embodiments. The signals pass between the electronics packages 106, 107 via the feed-through connector(s) 125.

As a result of the enhanced thermal performance of the electronics packages 106, 107 and the housing mount 108, the electronics assembly 100 may advantageously be mounted to be in direct physical contact with the drill collar 103, as opposed to the chassis 102 (although the electronics assembly may also be mounted to the chassis, if desired). More particularly, this electronics assembly 100 provides electromagnetic shielding properties and allows for mounting to the drill collar 103, which helps to reduce noise.

Figure 6:
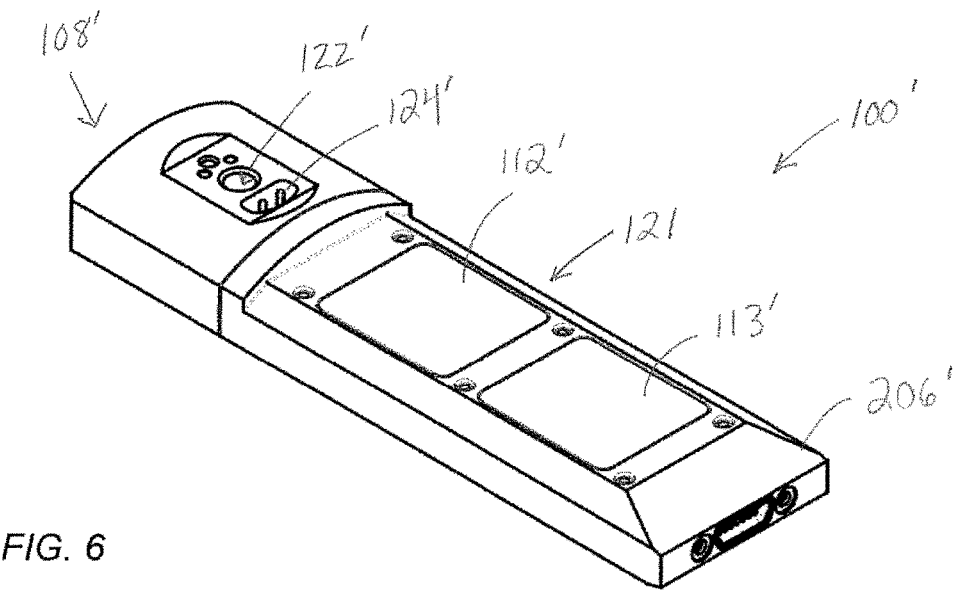
FIG. 6 is a perspective view of the top of another electronics assembly which may be used with the resistivity measurement tool of FIG. 2 (or in other LWD tools).
Figure 7:
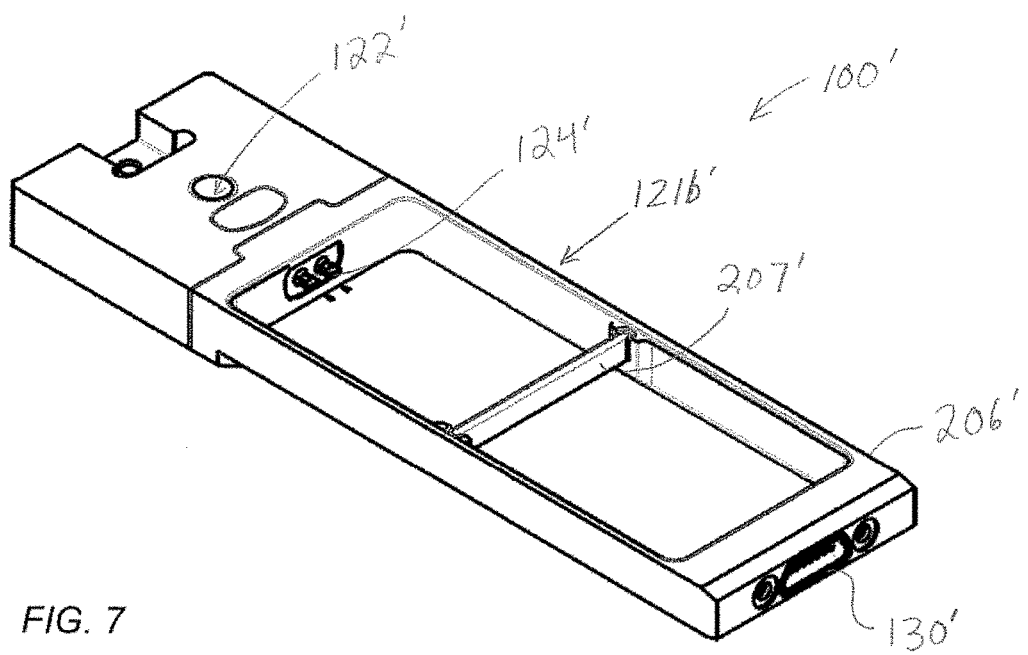
FIG. 7 is a perspective view of the bottom of the electronics assembly of FIG. 6.

Turning now to FIGS. 6 and 7, another electronics assembly 100' embodiment is now described. The electronics assembly 100' may be considered a cantilevered hybrid transmitter/receiver electronics package, in that there are not symmetrical packages 106, 107 as in the above-described embodiment, but rather a single housing 206' that is coupled with one side of the housing mount 108'. This cantilevered package configuration may be advantageous in that it may simplify the housing mount so that the above-described feed-through connector(s) 125 is not required. Low-level RF signal isolation may still be provided through the use of a septum 207' positioned between the RF and digital circuitry, if desired. Generally speaking, the material used for the septum 207' may have electromagnetic shielding properties (e.g., a metal) and may be welded to the electronic housing 206' as shown. The remaining components in FIGS. 6 and 7 are similar to those described above and are accordingly not separately discussed herein.

Another aspect is directed to a method for making the tools described above. The method includes positioning a drill collar surrounding a chassis and coupling the drill collar to the chassis using a port plug and with an electronics assembly positioned between the chassis and the drill collar. A plurality of radio frequency (RF) antennas are carried by the drill collar. The electronics assembly includes at least one multi-chip module (MCM) electronics package comprising a hermetically sealed electronics housing positioned between the chassis and the drill collar, and a substrate within the hermetically sealed electronics housing. RF transmitter circuitry is provided on the substrate to cooperate with at least one first RF antenna from among the plurality of RF antennas to transmit RF signals into the geological formation, and RF receiver circuitry is provided on the substrate to cooperate with at least one second RF antenna from among the plurality of RF antennas to receive RF signals from the geological formation. An electronics housing mount couples the hermetically sealed electronics housing with the port plug, the electronics housing mount having a passageway extending therethrough to receive the port plug.

Many modifications and other embodiments will come to the mind of one skilled in the art having the benefit of the teachings presented in the foregoing descriptions and the associated drawings. Therefore, it is understood that various modifications and embodiments are intended to be included within the scope of the appended claims.

That which is claimed is:

1. A tool for use in a borehole in a geological formation comprising:
   a chassis;
   a drill collar surrounding the chassis;
   a port plug coupled between the drill collar and the chassis;
   a plurality of radio frequency (RF) antennas carried by the drill collar;
   at least one multi-chip module (MCM) electronics package comprising
      a hermetically sealed electronics housing positioned between the chassis and the drill collar,
      a substrate within the hermetically sealed electronics housing,
      RF transmitter circuitry on the substrate to cooperate with at least one first RF antenna from among the plurality of RF antennas to transmit RF signals into the geological formation, and
      RF receiver circuitry on the substrate to cooperate with at least one second RF antenna from among the plurality of RF antennas to receive RF signals from the geological formation; and
   an electronics housing mount coupling the hermetically sealed electronics housing with the port plug, the electronics housing mount having a passageway extending therethrough to receive the port plug.

2. The tool of claim 1 wherein the electronics housing mount couples the at least one hermetically sealed electronics package in direct contact with the drill collar.

3. The tool of claim 1 wherein the at least one MCM electronics package comprises first and second MCM electronics packages; and wherein the electronics housing mount is coupled between the first and second MCM electronics packages.

4. The tool of claim 3 wherein said electronics housing mount further comprises at least one feed-through connector coupled between the first and second MCM electronics packages.

5. The tool of claim 1 wherein said at least one MCM electronics package further comprises control circuitry on the substrate to cooperate with the RF transmitter circuitry and the RF receiver circuitry to determine resistivity measurements for the geological formation.

6. The tool of claim 1 further comprising a septum within the hermetically sealed electronics housing to separate the RF receiver circuitry and the RF transmitter circuitry.

7. The tool of claim 1 wherein the substrate comprises a high temperature co-fired ceramic (HTCC).

8. The tool of claim 1 wherein the hermetically sealed electronics housing comprises at least one of titanium and Kovar.

9. An electronics assembly for a tool for use in a borehole in a geological formation, the tool comprising a chassis, a drill collar surrounding the chassis, a port plug coupled between the drill collar and the chassis, and a plurality of radio frequency (RF) antennas carried by the drill collar, the electronics assembly comprising:
- at least one multi-chip module (MCM) electronics package comprising
  - a hermetically sealed electronics housing to be positioned between the chassis and the drill collar,
  - a substrate within the hermetically sealed electronics housing,
  - RF transmitter circuitry on the substrate to cooperate with at least one first RF antenna from among the plurality of RF antennas to transmit RF signals into the geological formation, and
  - RF receiver circuitry on the substrate to cooperate with at least one second RF antenna from among the plurality of RF antennas to receive RF signals from the geological formation; and
- an electronics housing mount to couple the hermetically sealed electronics housing with the port plug, the electronics housing mount having a passageway extending therethrough to receive the port plug.

10. The electronics assembly of claim 9 wherein the electronics housing mount is to couple the at least one hermetically sealed electronics package in direct contact with the drill collar.

11. The electronics assembly of claim 9 wherein the at least one MCM electronics package comprises first and second MCM electronics packages; and wherein the electronics housing mount is coupled between the first and second MCM electronics packages.

12. The electronics assembly of claim 9 wherein said at least one MCM electronics package further comprises control circuitry on the substrate to cooperate with the RF transmitter circuitry and the RF receiver circuitry to determine resistivity measurements for the geological formation.

13. The electronics assembly of claim 9 further comprising a septum within the hermetically sealed electronics housing to separate the RF receiver circuitry and the RF transmitter circuitry.

14. The electronics assembly of claim 9 wherein the substrate comprises a high temperature co-fired ceramic (HTCC).

15. The electronics assembly of claim 9 wherein the hermetically sealed electronics housing comprises at least one of titanium and Kovar.

16. A method for making a tool for use in a borehole in a geological formation, the method comprising:
- positioning a drill collar surrounding a chassis and coupling the drill collar to the chassis using a port plug and with an electronics assembly positioned between the chassis and the drill collar;
- wherein a plurality of radio frequency (RF) antennas are carried by the drill collar;
- wherein the electronics assembly includes at least one multi-chip module (MCM) electronics package comprising a hermetically sealed electronics housing positioned between the chassis and the drill collar, a substrate within the hermetically sealed electronics housing, RF transmitter circuitry on the substrate to cooperate with at least one first RF antenna from among the plurality of RF antennas to transmit RF signals into the geological formation, and RF receiver circuitry on the substrate to cooperate with at least one second RF antenna from among the plurality of RF antennas to receive RF signals from the geological formation; and
- wherein an electronics housing mount couples the hermetically sealed electronics housing with the port plug, the electronics housing mount having a passageway extending therethrough receiving the port plug.

17. The method of claim 16 wherein positioning further comprising coupling the at least one hermetically sealed electronics package in direct contact with the drill collar.

18. The method of claim 16 wherein the at least one MCM electronics package comprises first and second MCM electronics packages; and wherein the electronics housing mount is coupled between the first and second MCM electronics packages.

19. The method of claim 16 wherein said at least one MCM electronics package further comprises control circuitry on the substrate to cooperate with the RF transmitter circuitry and the RF receiver circuitry to determine resistivity measurements for the geological formation.

20. The method of claim 16 wherein the at least one MCM module further comprises a septum within the hermetically sealed electronics housing to separate the RF receiver circuitry and the RF transmitter circuitry.

21. The method of claim 16 wherein the substrate comprises a high temperature co-fired ceramic (HTCC).

22. The method of claim 16 wherein the hermetically sealed electronics housing comprises at least one of titanium and Kovar.

* * * * *